United States Patent [19]

Webb et al.

[11] 3,979,468

[45] Sept. 7, 1976

[54] 4'-CHLORO-4-ETHYNYLBIPHENYL AND METHOD OF PREPARING SAME

[75] Inventors: Colin Frederick Webb; Barry John Price, both of London, England

[73] Assignee: Allen & Hanburys Limited, London, England

[22] Filed: Jan. 16, 1975

[21] Appl. No.: 541,393

[30] Foreign Application Priority Data

Jan. 31, 1974 United Kingdom................ 4531/74

[52] U.S. Cl..................... 260/649 DP; 260/515 A; 260/592; 260/599; 424/353
[51] Int. Cl.²......................................... C07C 25/26
[58] Field of Search....... 260/649 DP, 649 F, 649 R

[56] References Cited
UNITED STATES PATENTS 3,852,364 12/1964 Diamond.......................... 260/649 F

OTHER PUBLICATIONS

Safe, Chem. Abstracts 80, 119777a (1974), referred to in pp. 890F & 891F, vol. 80 index.

Primary Examiner—D. Horwitz
Attorney, Agent, or Firm—Bacon & Thomas

[57] ABSTRACT

Ethynylbiphenyl derivatives of the general formula (I):

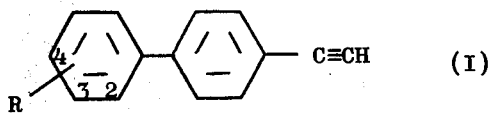

in which R represents a chlorine or bromine atom in the 2, 3 or 4 position. These compounds have anti-inflammatory activity.

3 Claims, No Drawings

4'-CHLORO-4-ETHYNYLBIPHENYL AND METHOD OF PREPARING SAME

This invention relates to novel 4-ethynylbiphenyl derivatives, to processes for the production thereof and to pharmaceutical compositions containing the same.

The present invention provides ethynylbiphenyl derivatives of the general formula (I):

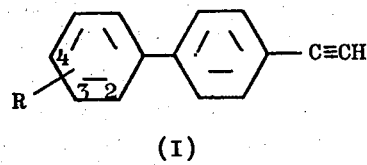

(I)

in which R represents a chlorine or bromine atom in the 2,3 or 4 position.

We have found that the compounds of the invention possesses useful anti-inflammatory activity. For example they have been shown to reduce the inflammation produced by an injection of carageenin into the hind paws of a rat (C.A. Winter, E.A. Risley and G.W. Nuss, Proc. Soc. Exper. Biol. Med. 111, 544, 1962), to reduce the inflammation produced in a rat by an injection of Freunds adjuvant (B.B. Newbold, Brit. J. Pharmacol. 21 127–136, 1963), and to inhibit the writhing produced in a mouse by the intraperitoneal injection of phenylquinone (L.C. Hendershot and J. Forsaith, J. Pharm. Exp. Ther. 125, 237–240, 1959).

A particularly preferred compound is the compound in which the group R is a chlorine atom in the 4 position.

Other compounds include:
2'-Chloro-4-ethynylbiphenyl
3'-Chloro-4-ethynylbiphenyl.
4'-Bromo-4-ethynylbiphenyl.

The dose of the active ingredient may be from 25 mg to 1000 mg per day depending on the age, weight and condition of the patient.

The compounds may be formulated for use in human and veterinary medicine for therapeutic purposes. The invention therefore provides pharmaceutical compositions comprising as one or more compounds according to the invention in association with a pharmaceutical carrier. Such compositions may be presented for use in a conventional manner with the aid of carriers, or excipients, and formulatory agents as required, and with or without supplementary medicinal agents. The carrier may be solid or a liquid. In the former instance the composition of the present invention may, for example, exist in the form of capsules, suppositories or tablets which may include binders and lubricants and which may be coated. If the carrier or diluent is a liquid the composition may be in the form of emulsions or suspensions. Advantageously the drug may be used in these compositions as a microfine solid. The compositions may be in unit dosage form each unit dosage containing the whole or a part of the per diem dose referred to above. Suitable unit dosage preparations are in particular tablets and capsules.

The compounds according to the invention may be prepared in a number of ways and these are described below.

In one process the compound of formula I may be prepared from the substituted acetophenone (II):

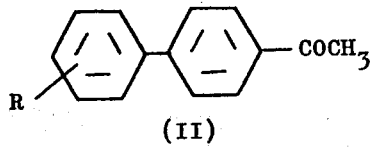

(II)

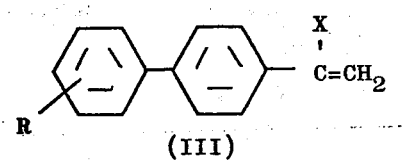

(III)

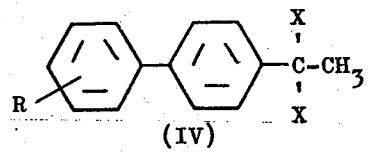

(IV)

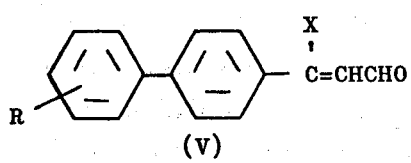

(V)

This process may be effected by several reagents that may give rise to different intermediates.

The reaction of (II) with a phosphorus halide e.g. $PCl_5$ in a suitable solvent such as toluene and at an elevated temperature e.g. above 50° gives an α-chlorovinylbiphenyl (III) plus a small amount of an α,α-dichloroethyl biphenyl (IV). Alternatively a mixture of an α-chlorovinyl biphenyl (III) and an α,α-dichloroethyl biphenyl (IV) may be obtained by treating the corresponding compound of formula (II) with a mixture of a phosphorus halide e.g. $PCl_5$ and phosphorus oxyhalide e.g. $POCl_3$. This reaction is preferably carried out with heating. Treatment of the α-chlorovinyl biphenyl (III) and/or the α,α-dichloroethyl biphenyl (IV) with a strong base affords the corresponding ethynylbiphenyl derivative (I). Suitable bases include sodamide, alkali-metal hydroxides e.g. potassium or sodium hydroxide or alkali metal alkoxides e.g. potassium ethoxide or potassium t-butoxide. When the acetophenone (II) is treated with a suitable Vilsmeier reagent such as that resulting from a phosphorus oxyhalide e.g. $POCl_3$ and dimethylformamide, and the resulting mixture is added to water the biphenyl acrolein (V, X = Cl) is formed. This acrolein may be converted into a compound of the invention by treatment with a base such as an alkali or alkaline hydroxide e.g. sodium hydroxide, preferably in a suitable solvent e.g. dioxan, at elevated temperatures (50°–100°).

An appropriate Vilsmeier reagent is one which introduces a formyl group.

In another process the biphenylaldehyde (VI) may be heated with malonic acid in a mixture of pyridine and piperidine to give the biphenylylacrylic acid (VII). Addition of bromine gives the dibromobiphenylylpropionic acid (VIII), which on treatment with a strong base affords a compound of the invention (I).

(VI) Ar-C6H4-CHO (with R on first ring)

(VII) Ar-C6H4-CH=CH-CO2H (with R on first ring)

(VIII) Ar-C6H4-CHBr-CHBrCO2H (with R on first ring)

The following Examples illustrate the invention:

EXAMPLE 1

4'-Chloro-4-ethynylbiphenyl

METHOD 1

4'-(4-Chlorophenyl)acetophenone (4.61 g), phosphoryl chloride (15 ml) and phosphorus pentachloride (5.0 g) were stirred at 80° for 3 hours. The excess of phosphoryl chloride was distilled off, and ethanol was added to the residue to give a pale brown solid (3.5 g). This solid and potassium hydroxide (9 g.) in ethanol (18 ml) were stirred and heated under reflux for 3 hours in an atmosphere of nitrogen. The solution was diluted with water (25 ml) and extracted with ethyl acetate (50 ml). The organic extract was washed with water, dried over magnesium sulphate and evaporated to leave a brown solid (2.5 g), that sublimed at 120° at 0.07 torr to give a white solid (2.1 g), m.p. 114°–118°.

METHOD 2

4'-(4-Chlorophenyl)acetophenone (24.8 g), phosphoryl chloride (80.7 ml) and phosphorus pentachloride (26.9 g) were stirred at 80° for 3 hours. The excess of phosphoryl chloride was distilled off and the residue was treated with ethanol. The pale brown solid (16.5 g) and potassium tertiary butoxide (69.7 g) in tertiary butanol (210 ml) were stirred and heated under reflux in an atmosphere of nitrogen for 3 hours. The cooled solution was diluted with water (300 ml) and extracted with ether (3 × 350 ml). The extracts were washed with water and dried over sodium sulphate, and the residue sublimed at 100°–110° at 0.1 torr to give a white solid m.p. 117°–121° (6.6 g). This crystallized from methanol to give material with m.p. 122°–123°.

METHOD 3

β,4'-Dichloro-4-biphenylacrolein

Phosphoryl chloride (44.5 g) was added dropwise with stirring to anhydrous dimethylformamide (130 ml) at 0°. A solution of 4'-(4-chlorophenyl)acetophenone (22.5 g) in dimethylformamide (100 ml) was added while the temperature was maintained below 10°. The solution was kept at 0° for 15 minutes and at room temperature for 18 hours and then it was poured onto ice. The solid was collected, washed with water, dried, and crystallized from cyclohexane. The product was a yellow solid, m.p. 115°–118°, (15.7 g).

In a similar manner:
β,3'-Dichloro-4-biphenylacrolein was prepared from 4'-(3-chlorophenyl)acetophenone
β,2'-Dichloro-4-biphenylacrolein was prepared from 4'-(2-chlorophenyl)acetophenone and
4'-Bromo-β-chloro-4-biphenylacrolein was prepared from 4'-(4-bromophenyl)acetophenone.

4'-Chloro-4-ethynylbiphenyl

Sodium hydroxide (N) (100 ml) was added rapidly to a solution of β,4'-dichloro-4-biphenylacrolein (12.2 g) in dioxan (160 ml) stirred at 60° in an atmosphere of nitrogen. After 1 hour the mixture was added to water (450 ml) and the precipitate was collected and dissolved in ethyl acetate. The solution was dried over magnesium sulphate, filtered and vaporated. The residue was sublimed at 120° at 1 torr to give a white solid, m.p. 120°–123°.

In a similar manner:
3'-Chloro-4-ethynylbiphenyl, a pale yellow oil, b.p. 108°/0.1 torr was obtained from β,3-dichloro-4-biphenylacrolein.
4-Bromo-4'-ethynylbiphenyl, m.p. 145°–150° was obtained from 4'-bromo-β-chloro-4-biphenylacrolein.
2'-Chloro-4-ethynylbiphenyl b.p. 126°–130°/0.6 torr was obtained from β,2'-dichloro-4-biphenylacrolein.

EXAMPLE 2

4-Bromo-4'-ethynylbiphenyl

A mixture of 4'-(p-bromophenyl)acetophenone (12.87 g) phosphorus pentachloride (12.25 g) and phosphoryl chloride (50 ml) was heated at 80° for 12 hours and evaporated. The residue was added to water and extracted with ether. The ethereal extract was washed with sodium bicarbonate solution and with water, dried and evaporated. A portion of the residue (11.3 g) was heated under reflux for 22 hours with a solution of potassium hydroxide (11.0 g) in tert-butanol. The mixture was cooled and was diluted with water and extracted with ether. The extracts were washed with water, dried over magnesium sulphate and evaporated to give a brown solid residue (4.92 g) which was sublimed at 120° at 0.2 torr to give a white solid. The solid was crystallised from methanol as white crystals and had m.p. 139°–143°.

In a similar manner:
2'-Chloro-4-ethynylbiphenyl b.p. 140°/0.1 torr was prepared from 4'-(2-chlorophenyl)acetophenone.

EXAMPLE 3

Tablets

To prepare 10,000, each containing 250 mg active ingredient

Mix together 2.5 kilos of powdered 4'-chloro-4-ethynylbiphenyl, 250 grammes of microcrystalline cellulose B.P.C. and 0.5 kilo of Encompress (Encompress is a proprietary brand of spray-dried calcium phosphate dihydrate), with 30 grammes of magnesium stearate.

Compress the mixed powder on a suitable tabletting machine to produce tablets each weighing about 330 mg and 10 mm in diameter.

EXAMPLE 4

Capsules

To prepare hard gelatin capsules each containing 100 mg active ingredient

Mix the required quantity of 4'-chloro-4-ethynylbiphenyl with sufficient microcrystalline cellulose to enable an adequate fill to be obtained in a No. 1 size hard gelatin capsule. Capsules of up to 250 mg can be prepared.

EXAMPLE 5

Oral Suspensions

Prepare a 1% gel of Carbopol 934 (Carbopol 934 is a proprietary brand of carboxyvinyl polymer), by dispersing the required quantity of Carbopol 934 in water and adjusting the pH to 7 with dilute sodium hydroxide solution. Carefully disperse in this gel sufficient finely powdered active ingredient so that each 5 ml contains 250 mg of 4'-chloro-4-ethynylbiphenyl. The gel is flavoured with suitable flavouring and sweetening agents and will contain a mixture of alkyl parahydroxybenzoate as preservative.

EXAMPLE 6

Suppositories

Suppositories can be prepared by dispersing microfine 4'-chloro-4-ethynylbiphenyl in a suitable suppository base such as Witepsol H15 and pouring into suitable moulds and cooling. Each suppository contains 200 mg of active ingredient.

Other compounds according to the invention may be incorporated in pharmaceutical compositions in a manner similar to that described for 4'-chloro-4-ethynylbiphenyl.

We claim:
1. 4'-chloro-4-ethynylbiphenyl.
2. A process for the preparation of 4'-chloro-4-ethynylbiphenyl which comprises treating $\beta$,4'-dichloro-4-biphenylacrolein with a base.
3. A process as claimed in claim 2 in which the $\beta$,4'-dichloro-4-biphenylacrolein is prepared by treating 4'-(4-chlorophenyl)acetophenone with a Vilsmeier reagent resulting from phosphorus oxychloride and dimethylformamide and adding the resulting mixture to water.

* * * * *